United States Patent [19]

Crooker et al.

[11] Patent Number: 5,246,625
[45] Date of Patent: Sep. 21, 1993

[54] STABILIZED 141B

[75] Inventors: Richard M. Crooker, Lehigh; Maher Y. Elsheikh, Tredyffrin, both of Pa.

[73] Assignee: EH Atochem North America, Inc., Philadelphia, Pa.

[21] Appl. No.: 34,049

[22] Filed: Mar. 22, 1993

Related U.S. Application Data

[60] Division of Ser. No. 978,956, Nov. 18, 1992, which is a continuation-in-part of Ser. No. 863,611, Apr. 6, 1992, abandoned.

[51] Int. Cl.$^5$ .......................... C08K 3/00; C09K 15/32
[52] U.S. Cl. ..................................... 252/350; 252/399; 252/400.1; 252/400.52; 521/98; 521/131; 521/92; 521/124

[58] Field of Search ..................... 252/350, 399, 400.1, 252/400.52; 521/98, 131, 92, 124

[56] References Cited

U.S. PATENT DOCUMENTS 4,948,479  8/1990  Brooks et al. ................. 204/158.21
5,135,680  8/1992  Crooker et al. ................. 521/84.1

Primary Examiner—Morton Foelak
Attorney, Agent, or Firm—Stanley A. Marcus; William D. Mitchell

[57] ABSTRACT

Storage-stable 141b prepared by contacting 141b with alumina at temperatures of about 0-100 degrees Centigrade, compositions containing the thus treated 141b, and uses thereof for the production of polyurethane and polyisocyanurate foams.

4 Claims, No Drawings

STABILIZED 141B

CROSS REFERENCE TO RELATED APPLICATIONS

This is a divisional of copending application Ser. No. 07/978,956 filed on Nov. 18, 1992, which in turn is a continuationin-part of then copending application Ser. No. 07/863,611, filed on Apr. 6, 1992 and now abandoned.

FIELD OF THE INVENTION

This invention relates to methods for rendering 1,1-dichloro-1-fluoroethane ("141b") storage-stable and, for blowing agent applications, stable against decomposition in polyol formulations or the corresponding polyurethane or polyisocyanurate foams made therefrom. More particularly, it relates to the use of alumina to stabilize 141b against decomposition during storage or use.

BACKGROUND OF THE INVENTION

Much attention has been focused on 141b in recent years as a replacement for CFC-11 (trichlorofluoromethane) as a foam blowing agent, as a solvent, and so forth. In the manufacture of 141b, however, such as by the reaction of hydrogen fluoride with 1,1,1-trichloroethane or vinylidene chloride ("VDC"), unwanted impurities such as unsaturated carbon compounds (including VDC) have been found to result. Thus, processes have been developed for removing VDC from 141b via photochlorination, such as disclosed in U.S. Pat. No. 4,948,479.

It has now been found, however, that even with such a purification procedure 141b can be unstable in storage, resulting in the formation of such unwanted by-products as phosgene. Thus, the industry is in need of a means for producing storage-stable 141b.

As noted in U.S. Pat. No. 5,135,680, 141b also has stability problems in blowing agent applications. As there stated, "Polyurethane and polyisocyanurate foams are conventionally prepared by reacting an organic polyisocyanate (including diisocyanate) 'A-side' component with a 'B-side' polyol premix component containing organic polyol, blowing agent, surfactant, catalyst, and possibly other additives such as flame retardants, antioxidants, and U.V. stabilizers. These A-side and B-side components may be purchased by the end-user in separate containers and stored for later use. Since decomposition of the HCFC blowing agents has been observed in the B-side premixes during storage and during the process of making the foam, HCFC compositions inhibited against such decompositions would be highly desirable. For example, the preferred 141b blowing agent has been observed to decompose during the foam-making process to up to about 1%, depending on the formulation and reaction conditions, of various decomposition products of which by far the predominant product is 1-chloro-1-fluoroethylene ("1131a"). Inhibition of such decomposition is desired both because of toxicity concerns and because the decomposition is accompanied by the formation of equivalent amounts of acid which in turn causes catalyst deactivation."

SUMMARY OF THE INVENTION

This invention is directed to a method for rendering 141b storage-stable which comprises contacting said 141b with alumina at a temperature of from about 0 to 100 degrees Centigrade (preferably about 20-40 degrees); to the resulting storage-stable 141b compositions comprised of 141b alone or 141b in a premix composition containing a polyol and, optionally, other ingredients such as surfactants, catalysts, and flame retardants; to foamable compositions containing 141b, polyol, and polyisocyanate; to methods of making foam from such compositions; and to the resulting foams.

DETAILED DESCRIPTION OF THE INVENTION

It has now been found that 141b is stabilized against decomposition during storage by treatment with alumina. Particularly surprising is the discovery that alumina is effective both to remove any phosgene already formed and to prevent its reoccurrence during storage. In contrast thereto, the removal of phosgene from 141b with a sodium hydroxide solution does not prevent the reoccurrence of phosgene during storage. Equally surprising is the discovery that the thus-treated 141b is stabilized, without the need for added inhibitors, against the decomposition into 1131a for blowing agent applications.

While any alumina may be used and no specific crystalline structure is required, it is preferred to use alumina having a high surface area such as is found in activated alumina. Examples 1 and 2 below demonstrate the effectiveness of a variety of commercially available activated aluminas.

The 141b can be treated batchwise or continuously, such as by passing the 141b over a bed of alumina.

The temperature can range from about 0 to about 100 degrees Centigrade, preferably from about 20 to about 40 degrees. Higher temperatures can lead to the formation of unwanted decomposition products, while at lower temperatures the rate of adsorption of phosgene can be significantly slower.

The contact time can vary from a matter of seconds to 48 hours or more. The optimum time varies with the method of contact, the size of the alumina bed, the 141b flow rate, the phosgene level (if any) in the 141b, and so on, as can readily be determined by one skilled in the art.

The method is demonstrated below for treating 141b in the liquid state, but should also have utility for treating 141b while in the gas state.

The invention was illustrated in the following examples using a "pure" 141b made by a process such as taught in U.S. Pat. No. 4,948,479, i.e., by reacting hydrogen fluoride and 1,1,1-trichloroethane, photochlorinating, and distilling. Typical product analyses are given in Table 1 of that patent. The invention is, however, equally applicable to 141b made by other processes, such as by reacting HF with vinylidene chloride.

Example 1—A "purified" liquid 141b (120 grams) in which phosgene had already formed upon storage to a level of about 12 ppm was mixed batchwise with 50 grams each of a variety of commercially available, dried, activated aluminas (La Roche's A201 and A204, Alfa Thiokol's gamma alumina, Harshaw's Al 4126, and Alcoa's 5×7 LDS) for one-half hour at room temperature (about 22 degrees Centigrade). Analysis for phosgene, which was carried out spectrophotometrically using 4-(p-nitrobenzyl)-pyridine, showed that in each case the phosgene was reduced to less than 3 ppm.

Example 2—In this example 141b having a level of about 14 ppm of phosgene was fed at a rate of 20 ml/min. at room temperature through beds (85 grams each) of a variety of dried, activated aluminas (La Roche's 210, 202, 204.1, and 204.4) loaded in a 100 ml burette. The contact time was about 5.3 minutes. For each of the 4 aluminas tested, analysis of the treated 141b showed phosgene levels of less than 0.4 ppm.

Example 3—The alumina-treated 141b from Example 2 was subjected to U.V. irradiation for four hours in the presence of air since five hours of such irradiation have been found to simulate one year of aging at ambient temperature. Analysis showed no evidence of phosgene formation. In contrast, when untreated 141b was irradiated, 20 ppm of phosgene were formed.

Example 4—Example 2 with La Roche 204.4 alumina was essentially repeated except that only 8 grams of activated alumina was used and contact times of 0.53 and 0.26 minute were tried. At 0.53 minute the phosgene was again reduced to 0.4 ppm or less; at 0.26 minute the phosgene was reduced to about 1 ppm.

For blowing agent applications the 141b can also be incorporated into compositions containing a polyol or a fully formulated B-side formulation containing a polyol, catalyst, surfactant, and, optionally, other additives. Typical polyols are, for example, Stepanol PS 2502A, an aromatic polyester polyol sold by the Stepan Company; Terate 203, an aromatic polyester polyol sold by Cape Industries; Pluracol Polyol 975, a sucrose-based polyol sold by BASF; Poly-G 71-530, a polyether polyol sold by Olin; and Quadrol, an amine-based polyol supplied by BASF. Typical catalysts include Potassium HEX-CEM, a potassium octoate sold by Mooney Chemicals; Polycat 41, an N,N,N-tri(dimethylaminopropyl)cyclohexatriazine sold by Air Products; Polycat 8, an N,N-dimethylcyclohexylamine sold by Air Products; Dabco TMR-30, a 2,4,6-tri-(dimethylaminomethyl)phenol supplied by Air Products; and Dabco K-15, a potassium 2-ethylhexoate in diethylene glycol supplied by Air Products. A typical surfactant is Dow Corning 193, a silicone polymer. A typical A-side component is Mondur E-489, an aromatic diisocyanate supplied by Miles Inc , or Lupranate M20S, a polymethylene-diisocyanate supplied by BASF.

Example 5—Polyurethane foams were prepared using untreated 141b and 141b which had been treated with La Roche 204.4 alumina at room temperature for 5 minutes In each case the foam was prepared by stirring a formulation containing polyol (100g of Stepanol PS 2502A), 141b (25.8g), surfactant (1.51g of Dow Corning 193), catalyst (2.82g of Potassium HEX-CEM and 0.7g of Polycat 41), and diisocyanate (127.2g of Mondur E-489). The hot foam was left to cool to room temperature for about one hour After curing the foam at 250 degrees Fahrenheit for 20 hours, the foam cell gas was analyzed by crushing a sample cut from the center of the foam and injecting the released gas mixture directly to a gas chromatograph. The cell gas of the foam made from the untreated 141b was found to contain 2587 ppm of 1131a, while the cell gas of the foam made from alumina-treated 141b contained only 820 ppm of 1131a.

What is claimed is:

1. Storage-stable 1,1-dichloro-1-fluoroethane resulting from contacting 1,1-dichloro-1-fluoroethane with alumina at a temperature of from about 0 to about 100 degrees Centigrade.

2. Storage-stable 1,1-dichloro-1-fluoroethane as in claim 1 wherein the alumina is activated alumina.

3. A composition comprising a polyol and the storage-stable 1,1-dichloro-1-fluoroethane of claim 1.

4. A composition comprising a polyol and the storage-stable 1,1-dichloro-1-fluoroethane of claim 2.

* * * * *